US00PP14141P29

(12) United States Plant Patent
Godard

(10) Patent No.: US PP14,141 P2
(45) Date of Patent: Sep. 16, 2003

(54) NOLANA PLANT NAMED 'NOLGOLD'

(75) Inventor: Claude Godard, Dijon (FR)

(73) Assignee: Floanova Ltd., Foxley (GB)

( * ) Notice: Subject to any disclaimer, the term of this patent is extended or adjusted under 35 U.S.C. 154(b) by 0 days.

(21) Appl. No.: 10/162,988

(22) Filed: Jun. 5, 2002

(51) Int. Cl.[7] ..... A01H 5/00

(52) U.S. Cl. ..... Plt./263

(58) Field of Search ..... Plt./263

(56) References Cited

PUBLICATIONS

UPOV–TOM GTITM, Plant Variety Database, 2003/01, GTI Jouve Retrieval Software, Citation for Nolana 'Nolgold'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Nolana plant named 'Nolgold', characterized by its uniform, low-growing, cascading and outwardly spreading plant habit; freely and continuous branching habit; short internodes; dense and bushy plant growth habit; freely flowering habit; and blue violet and white bi-colored flowers.

1 Drawing Sheet

Botanical classification cultivar designation: Nolana×hybrida cultivar Nolgold.

BACKGROUND OF THE INVENTION

The present Invention relates to a new and distinct cultivar of Nolana plant, botanically known as Nolana×hybrida, and hereinafter referred to by the name 'Nolgold'.

The new Nolana is a product of a planned breeding program conducted by the Inventor in Dijon, France. The objective of the breeding program is to create new compact Nolanas with numerous flowers with attractive flower colors.

The new Nolana originated from a cross-pollination made by the Inventor in May, 1995 of an unidentified selection of *Nolana paradoxa*, not patented, as the female, or seed parent, with an unidentified selection of *Nolana humifusa*, not patented, as the male, or pollen parent. The new Nolana was selected as a single flowering plant from the resulting progeny from the cross-pollination by the Inventor in a controlled environment in Dijon, France.

Asexual reproduction of the new cultivar by terminal cuttings taken in Foxley, Norfolk, United Kingdom since November, 1998 has shown that the unique features of this new Nolana are stable and reproduced true to type in successive generations.

SUMMARY OF THE INVENTION

Plants of the cultivar Nolgold have not been observed under all possible environmental conditions. The phenotype may vary somewhat with variations in environment such as temperature and light intensity without, however, any variance in genotype.

The following traits have been repeatedly observed and are determined to be the unique characteristics of 'Nolgold'. These characteristics in combination distinguish 'Nolgold' as a new and distinct cultivar:

1. Uniform, low-growing, cascading and outwardly spreading plant habit.
2. Freely and continuous branching habit; short internodes; dense and bushy plant growth habit.

3. Freely flowering habit.
4. Blue violet and white bi-colored flowers.

Plants of the new Nolana can be compared to plants of the female parent, the unidentified selection of *Nolana paradoxa*. In side-by-side comparisons conducted in Foxley, Norfolk, United Kingdom, plants of the new Nolana differed from plants of the female parent in the following characteristics:

1. Plants of the new Nolana were more vigorous than plants of the female parent.
2. Plants of the new Nolana had smaller leaves than plants of the female parent.
3. Plants of the new Nolana had larger flowers than plants of the female parent.
4. Flower color of plants of the new Nolana was lighter than flower color of plants of the female parent.

Plants of the new Nolana can be compared to plants of the male parent, the unidentified selection of *Nolana humifusa*. In side-by-side comparisons conducted in Foxley, Norfolk, United Kingdom, plants of the new Nolana differed from plants of the male parent in the following characteristics:

1. Plants of the new Nolana were more vigorous than plants of the male parent.
2. Plants of the new Nolana had larger flowers than plants of the male parent.

Plants of the new Nolana can be compared to plants of the Nolana cultivar Bluebird, not patented. In side-by-side comparisons conducted in Foxley, Norfolk, United Kingdom, plants of the new Nolana differed from plants of the cultivar Bluebird in the following characteristics:

1. Plants of the new Nolana were more vigorous than plants of the cultivar Bluebird.

2. Plants of the new Nolana had shorter internodes than plants of the cultivar Bluebird.
3. Plants of the new Nolana flowered for a longer period of time than plants of the cultivar Bluebird.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Nolana.

The photograph at the top of the sheet comprises a side perspective view of three typical flowering plants of 'Nolgold' grown in a 25-cm container.

The photograph at the bottom of the sheet comprises a close-up view of typical developing flower buds and flowers; upper, lateral and lower surfaces of opened flowers; and upper and lower surfaces of typical leaves of 'Nolgold'.

DETAILED BOTANICAL DESCRIPTION

The aforementioned photographs and following observations and measurements describe plants grown in Lompoc, Calif., under commercial practice during the winter and spring in a polycarbonate-covered greenhouse with day temperatures about 18 to 24° C., night temperatures about 16 to 18° C., and light levels about 4,000 to 8,000 foot-candles. Three cuttings were planted in 25-cm containers and plants were grown for about 13 weeks. In the following description, color references are made to The Royal Horticultural Society Colour Chart, 1995 Edition, except where general terms of ordinary dictionary significance are used.

Botanical classification: Nolana×hybrida cultivar Nolgold.

Parentage:

*Female parent.*—Unidentified selection of *Nolana paradoxa*, not patented.

*Male parent.*—Unidentified selection of *Nolana humifusa*, not patented.

Propagation:

*Type cutting.*—Terminal vegetative cuttings.

*Time to initiate roots.*—About 10 days at 20° C.

*Time to develop roots.*—About 21 days at 20° C.

*Root description.*—Fine, fibrous.

Plant description:

*Form.*—Annual flowering plant; uniform, low-growing, cascading and outwardly spreading plant habit; plants eventually becoming hemispherical to spherical in shape. Freely and continuously branching habit with about five to six primary branches per plant with lateral branches forming potentially at every node; short internodes; dense and bushy plant growth habit. Moderately vigorous.

*Usage.*—Appropriate for hanging baskets, window boxes, patio containers and landscape applications.

*Plant height.*—About 20 cm.

*Plant diameter, single plant.*—About 24 cm.

*Lateral branches.*—Length: About 50 cm. Diameter: About 3 mm. Internode length, vegetative branches: About 2.3 cm. Internode length, flowering branches: About 3.5 cm. Strength: Moderately strong. Texture: Smooth, glabrous. Color: 144B.

*Foliage description.*—Arrangement: Before flowering, alternate; after flowering, opposite; simple. Length: About 2.8 cm. Width: About 1.6 cm. Shape: Elliptic. Apex: Acute. Base: Cuspidate with obtuse tendencies. Margin: Entire. Texture, upper and lower surfaces: Smooth, glabrous. Venation pattern: Pinnate, arcuate. Color: Young and fully expanded foliage, upper surface: 147A. Young and fully expanded foliage, lower surface: 147B. Venation, upper surface: 147D. Venation, lower surface: 144D. Petiole length: About 6 mm. Petiole diameter: About 3 mm. Petiole color, upper and lower surfaces: 144D.

Flower description:

*Flower type and habit.*—Salverform flowers; single, axillary. Flowers face mostly upward or outward and are held above the foliage. Flowers persistent. Flowers not fragrant.

*Quantity of flowers.*—Very freely flowering, typically about 5 open flowers and flower buds lateral branch.

*Natural flowering season.*—Spring until frost in the autumn; flowering continuous during the flowering period.

*Flower longevity on the plant.*—About two days in the landscape.

*Flower diameter.*—About 4 cm.

*Flower depth (height).*—About 1.5 cm.

*Flower throat diameter.*—About 1.5 cm.

*Flower tube length.*—About 1.5 cm.

*Flower buds (showing color).*—Length: About 1.7 cm. Diameter: About 7 mm. Shape: Elongated oblong. Color: 85C.

*Corolla.*—Arrangement/appearance: Single whorl of five petals, fused into flared trumpet. Petal length from throat: About 1.3 cm. Petal width: About 2 cm. Petal shape: Fan-shaped. Petal apex: Rounded with acute tendencies. Petal margin: Entire, ruffled. Petal texture, upper and lower surfaces: Smooth, satiny. Color: Petal, upper surface, when opening: 96C. Petal, lower surface, when opening: 97B. Petal, upper surface, fully opened: 96D; towards throat, 155D to 157A; hair-like striations radiating from the throat, 95A; color fading to 97A with subsequent development. Petal, lower surface, fully opened: 97B. Flower throat: 95A. Flower tube: 97B to 97D.

*Sepals.*—Arrangement/appearance: Single whorl of five sepals fused at base. Length: About 1.2 cm. Width: About 4 mm. Shape: Elliptic. Apex: Acute. Base: Fused. Margin: Entire. Texture, upper and lower surfaces: Smooth, glabrous. Color, upper surface: 144D. Color, lower surface: 144C.

*Peduncles.*—Length: About 3.6 cm. Width: About 1.5 mm. Angle: About 45 to 90° to the stem. Strength: Moderately strong. Texture: Smooth, glabrous. Color: 144C.

*Reproductive organs.*—Stamens: Quantity per flower: Five, adnate to base of corolla tube. Anther shape: Ovoid. Anther length: Less than 1 mm. Anther color: 92A. Pollen amount: Scarce. Pollen color: 92A. Pistils: Quantity per flower: One. Pistil length: About 1 cm. Stigma shape: Anvil-shaped, rounded. Stigma color: 147A. Style length: About 8 mm. Style color: 150C. Ovary color: 150D.

*Seed/fruit.*—Seed and fruit production has not been observed.

Disease/pest resistance: Plants of the new Nolana have not been noted to be resistant to pathogens or pests common to Nolana.

It is claimed:

1. A new and distinct cultivar of Nolana plant named 'Nolgold', as illustrated and described.

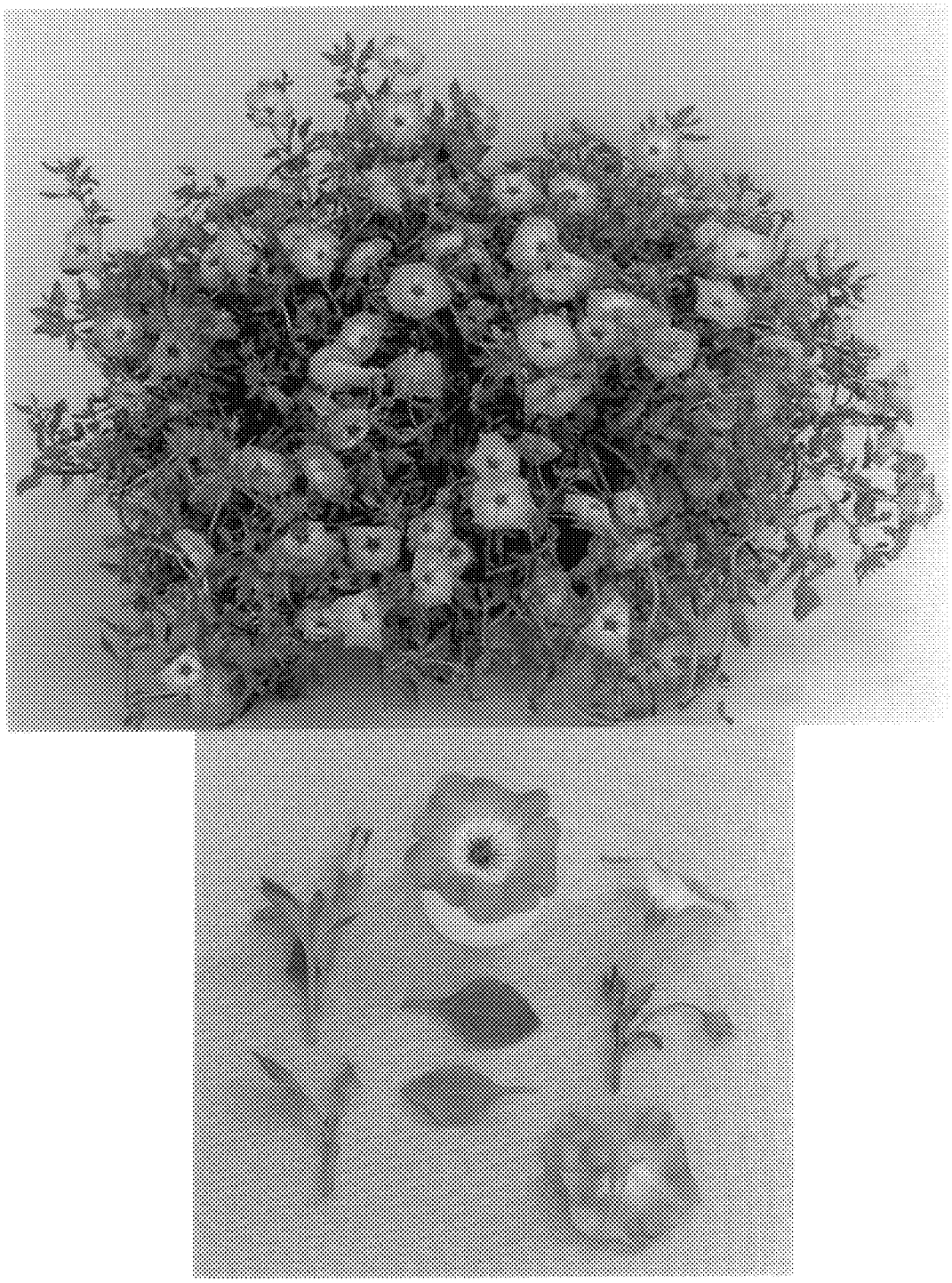

* * * * *